United States Patent [19]

Dreikorn et al.

[11] 3,979,387

[45] Sept. 7, 1976

[54] 4,5-DIHYDROTETRAZOLO(1,5-A)QUINOXALINES

[75] Inventors: Barry A. Dreikorn; Thomas D. Thibault, both of Indianapolis, Ind.

[73] Assignee: Eli Lilly and Company, Indianapolis, Ind.

[22] Filed: June 10, 1975

[21] Appl. No.: 585,533

[52] U.S. Cl. ............................ 260/250 Q; 424/250; 71/92
[51] Int. Cl.² ...................................... C07D 487/04
[58] Field of Search ................................ 260/250 Q

[56] References Cited
UNITED STATES PATENTS

| | | | |
|---|---|---|---|
| 3,624,093 | 11/1971 | Sulkowski | 260/288 |
| 3,639,406 | 2/1972 | Reimlinger et al. | 260/288 |
| 3,764,631 | 10/1973 | Dreikorn | 260/288 |
| 3,775,417 | 10/1973 | de Ruiter | 260/288 |
| 3,835,137 | 10/1974 | Wagner | 424/251 |
| 3,839,569 | 10/1974 | Dreikorn | 424/258 |
| 3,891,653 | 6/1975 | Dreikorn | 260/288 |
| 3,911,127 | 10/1975 | Shragia | 424/250 |
| 3,914,228 | 10/1975 | Edamura | 260/250 AC |

FOREIGN PATENTS OR APPLICATIONS

| | | |
|---|---|---|
| 803,098 | 3/1973 | Belgium |
| 2,249,350 | 4/1974 | Germany |
| 1,001,067 | 8/1965 | United Kingdom |

OTHER PUBLICATIONS

Shiho et al., J. Amer. Chem. Soc. 82, 4044–4054 (1960).
Koshel et al., Chem. Abs. 73, 120589c (1970).
Huisgen et al., Justus Leibigs Ann. Chem. 610, 57–66 (1957).

*Primary Examiner*—Alton D. Rollins
*Assistant Examiner*—Mark L. Berch
*Attorney, Agent, or Firm*—Joseph A. Jones; Everet F. Smith

[57] ABSTRACT

A class of new 4,5-dihydrotetrazolo[1,5-a]quinoxalines are useful for protecting plants from foliar phytopathogens.

6 Claims, No Drawings

4,5-DIHYDROTETRAZOLO(1,5-A)QUINOXA-LINES

BACKGROUND OF THE INVENTION

This invention belongs to the field of agricultural chemistry, and provides to the art new compounds useful for protecting plants from, and reducing the adverse effects of, foliar phytopathogens. The protection of plants from such phytopathogens is of paramount importance in agriculture. Nearly every ornamental and crop plant is injured by diseases caused by foliar phytopathogens. Many important crops cannot be economically raised without chemically protecting the plant from such phytopathogens. Some of the earliest achievements of agricultural chemistry were in the field of plant protection, and the art continues to search vigorously for new and improved plant protective agents.

Some prior publications are important to an understanding of the background of this invention. Dreikorn, U.S. Pat. Nos. 3,764,681 and 3,839,569, disclosed the fungicidal efficacy of tetrazolo[1,5-a]quinolines, dihydrotetrazolo[1,5-a]quinolines and s-triazolo[4,3-a]quinolines. Belgian Pat. No. 803,098 and West German Offenlegungsschrift No. 2,249,350 disclosed fungicidal use of certain imidazoquinoxalines.

The hydrogenation of multiple-fused-ring systems has been illustrated by, for example, de Ruiter, U.S. Pat. No. 3,775,417, by Sulkowski, U.S. Pat. No. 3,624,093, and by Reimlinger, U.S. Pat. No. 3,639,406. The reader is also referred to Huisgen, *Justus Leibigs Ann. Chem.* 610, 57–66 (1957), C.A. 52, 9125(d) (1958), who described dihydrotetrazoloquinolines and related compounds.

British Pat. No. 1,001,067 shows 4,5-dihydrotetrazoloquinolines, used as photographic chemicals, U.S. Pat. No. 3,835,137, of Wagner, shows dihydrotetrazoloquinazolines to be useful fibrinolytic agents.

SUMMARY OF THE INVENTION

This invention provides new compounds of the formula

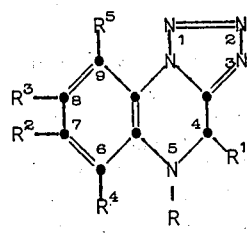

wherein
R and $R^1$ independently represent hydrogen, ethyl or methyl;
$R^2$, $R^3$, $R^4$ and $R^5$ independently represent ethyl, methyl, chloro, fluoro, bromo or hydrogen;
provided that at least four of R, $R^1$, $R^2$, $R^3$, $R^4$ and $R^5$ represent hydrogen.

The invention also provides a new method of reducing the adverse effects of foliar phytopathogens which comprises contacting the phytopathogens on the foliage of plants with an effective phytopathogen-inhibiting amount of a compound described above.

DESCRIPTION OF THE PREFERRED EMBODIMENT

The compounds named below are typical of the compounds of this invention. It will be understood that the named compounds do not bound the scope of the invention, but are presented merely to help those of chemical skill to understand the invention.

4,5-dihydro-7-methyltetrazolo[1,5-a]quinoxaline
5-methyl-4,5-dihydrotetrazolo[1,5-a]quinoxaline
4,5-dihydro-5-ethyl-7-methyltetrazolo[1,5-a]quinoxaline
8-bromo-4,5-dihydrotetrazolo[1,5-a]quinoxaline
4,5-dihydro-9-methyltetrazolo[1,5-a]quinoxaline
7-chloro-4,5-dihydrotetrazolo[1,5-a]quinoxaline
4,5-dihydro-8-methyltetrazolo[1,5-a]quinoxaline
4,5-dihydro-7-fluoro-6-methyltetrazolo[1,5-a]quinoxaline
4-ethyl-4,5-dihydrotetrazolo[1,5-a]quinoxaline
4,5-dihydro-6-fluorotetrazolo[1,5-a]quinoxaline
9-bromo-4,5-dihydrotetrazolo[1,5-a]quinoxaline
6,9-dibromo-4,5-dihydrotetrazolo[1,5-a]quinoxaline
4,5-dihydro-5-ethyltetrazolo[1,5-a]quinoxaline
6-chloro-4,5-dihydro-4-methyltetrazolo[1,5-a]quinoxaline
4,5-dihydro-8-ethyltetrazolo[1,5-a]quinoxaline
4-methyl-4,5-dihydro-7-fluorotetrazolo[1,5-a]quinoxaline
9-chloro-4,5-dihydrotetrazolo[1,5-a]quinoxaline
4,5-dihydro-8-fluorotetrazolo[1,5-a]quinoxaline The preferred compounds of this invention, which are also the compounds with which the method is preferably carried out, are 4,5-dihydro-5-methyltetrazolo[1,5-a]quinoxaline, 4,5-dihydro-6-methyltetrazolo[1,5-a]quinoxaline, 4,5-dihydrotetrazolo[1,5-a]quinoxaline, 4,5-dihydro-4-methyltetrazolo[1,5-a]quinoxaline, and 4,5-dihydro-4,6-dimethyltetrazolo[1,5-a]quinoxaline.

It will be understood that the tetrazole moiety of the compounds could be at times in the tautomeric azide form. Spectral evidence indicates that the compounds are primarily in the tetrazole form and remain so under the conditions at which the compounds have usually been handled. However, some conditions of solvent, temperature and pressure could shift the equilibrium to the azide form. Chemists will recognize that the compounds are the same entities, whether they are in the tetrazole or azide form.

The compounds of this invention are readily obtained. Some teaching of the synthesis of the compounds, as well as specific preparative examples, will be given to assure that organic chemists can obtain the compounds. In general, the compounds are obtained by the hydrogenation of the 4,5 bond of the corresponding tetrazolo[1,5-a]quinoxalines.

The reader is referred to Shiho et al., "Studies on Compounds Related to Pyrazine", *J. Am. Chem. Soc.* 82, 4044–54 (1960), for general discussion of the synthesis of the starting compounds.

The starting compounds are made from appropriately substituted 2-chloroquinoxalines, which are obtainable by well-known processes, such as those discussed by Platt, "2-Hydroxy- and 2-Amino-Derivatives of 6- and 7-Methylquinoxaline", *J. Chem. Soc.*, 1310–13 (1948).

In general, the tetrazolo[1,5-a]quinoxalines are formed by the reaction of the 2-chloroquinoxalines with azide ion in acidic aqueous ethanol. See U.S. Pat. No. 3,764,681 on the preparation of related tetrazoloquinolines. From 1 to 8 hours of reaction time at the reflux temperature is usually adequate to form the product in high yield. When the desired product has a 4-halogen substituent, however, it is best to convert the starting compound to the corresponding 2-hydrazinoquinoxaline and react the intermediate with nitrous acid in acetic acid at low temperature.

The chloroquinoxalines are most conveniently made by the reaction of an appropriately substituted o-phenylenediamine with glyoxylic acid in ethanol to form a 2-quinoxalinone. (Platt, supra, shows the compound as a quinoxalinol.) If the phenylenediamine is asymmetrically substituted, as would be the case if, for example, a product having a 7- or 6-substituent were to be made, a mixture of isomeric quinoxalinones will be made. The isomers may be separated at that point, or may be carried through the process as a mixture, and the products separated at any convenient point in the process. Whether the isomers are separated or not, the quinoxalinone is reacted with a chlorinating agent such as $POCl_3$ to form the corresponding 2-chloroquinoxaline.

The problem of mixtures of isomeric intermediate compounds can be avoided by an unambiguous method of synthesizing the intermediates. For example, a route can be used which reacts an appropriately substituted o-nitroaniline with cyanoacetic acid to form the correspondingly ring-substituted α-cyano-o-nitroacetanilide. That compound is reacted with base in pyridine to form the 3,4-dihydro-3-oxo-2-quinoxalinecarbonitrile, 1-oxide, which is reduced to the desired 2-quinoxalinone with sodium dithionite. See Ahmad et al., "Quinoxaline Derivatives III", Tetra. 20, 1107–12 (1964), and "Quinoxaline Derivatives IV", Tetra. 21, 861–65 (1965).

The 4-substituent of the products is derived from a corresponding substituent on the glyoxylic acid from which the intermediate is made. The 5-substituent is added to the compound, before or after the hydrogenation step, by alkylation with an alkylating agent such as an alkyl halide, tosylate, or sulfate, a trialkyl oxonium salt, or a Michael acceptor in the presence of an alkali metal hydride.

Hydrogenation of the 4,5 double bond is accomplished by hydrogenation of the compound in the presence of a catalyst. Precious metal catalysts such as platinum and palladium are used, particularly in the form of metallized supports such as platinized and palladized charcoal and calcium carbonate. Lithium aluminum hydride can also be used. The hydrogenation is accomplished at moderate pressures of from 1 to 5 atmospheres and at easily-handled temperatures in the general range of room temperature, as from 5° to 50°C. Economically acceptable yields are obtained by reaction times of from 2 to 24 hours.

The first 3 preparative examples illustrate the preparation of the starting tetrazolo[1,5-a]quinoxalines.

EXAMPLE 1

6-methyltetrazolo[1,5-a]quinoxaline

A solution was made of 0.5 g. of 2-chloro-5-methylquinoxaline, 10 ml. of 0.1N HCl and 0.6 g. of sodium azide in 35 ml. of denatured ethanol. The reaction mixture was stirred for 6 hours at reflux temperature. When the mixture was allowed to cool, the product, 6-methyltetrazolo[1,5-a]quinoxaline, crystallized in 91 percent yield and was separated by filtration. The product had a melting point of 160°–62°C., and was identified by nuclear magnetic resonance analysis and elemental microanalysis, the results of which were as follows.

|   | Theoretical | Found |
|---|---|---|
| C | 58.37% | 58.39% |
| H | 3.81 | 3.66 |
| N | 37.82 | 35.75 |

EXAMPLE 2

9-methyltetrazolo[1,5-a]quinoxaline

A solution was made of 10 g. of 2-methyl-6-nitroaniline and 5.8 g. of cyanoacetic acid in 200 ml. of benzene, and 14 g. of phosphorus pentachloride was added in small portions to the mixture. After the addition was complete, the mixture was stirred at 60°C. for four hours. The reaction mixture was then allowed to cool, and the intermediate product, α-cyano-6'-nitro-o-acetotoluidide, crystallized spontaneously. It was separated by filtration and was washed with benzene. The yield was 13.3 g., and the melting point, after recrystallization from ethanol, was 192°–93.5°C.

Ten g. of the above intermediate product was stirred in a mixture of 50 ml. of pyridine and 50 ml. of 1N NaOH at room temperature for 3 hours. The reaction mixture was then made acidic and 8.5 g. of 3,4-dihydro-5-methyl-3-oxo-2-quinoxalinecarbonitrile, 1-oxide, precipitated from the mixture. The product was recrystallized from ethanol, after which the melting point of the intermediate product was 294°C.

Five g. of the above intermediate product and 10 g. of sodium dithionite were stirred at reflux temperature in 200 ml. of water containing a few milliliters of ethanol. The starting compound soon dissolved, and the solution was then filtered hot, acidified and concentrated under vacuum. The residue was dissolved in 1N NaOH and filtered. The product, 8-methylquinoxaline-2(1H)-one, precipitated from the filtrate upon acidification. The yield was 3.3 g. and the melting point of the product was 267°–70°C.

A 2.2 g. portion of the above intermediate product was stirred with 30 ml. of phosphorus oxychloride as the temperature was brought to reflux and maintained at that temperature for 10 minutes. The cooled solution was concentrated and the resulting oil was dissolved in ethyl acetate. The solution was filtered and washed with 5 percent aqueous sodium carbonate until the washings were alkaline, and then washed with water. The organic phase was dried over sodium sulfate and evaporated to obtain an oil which solidified upon standing.

The crude 3-chloro-5-methylquinoxaline obtained in the step above was stirred for 3 hours at reflux temperature in 75 ml. of ethanol containing 1.8 g. of sodium azide and 20 ml. of 1N HCL. When the reaction mixture was cooled, the product precipitated as needles. Recrystallization of the product from ethanol produced highly purified 9-methyltetrazolo[1,5-a]quinoxaline, m.p. 166°–68°C. The product was identified by NMR analysis and elemental microanalysis.

| | Theoretical | Found |
|---|---|---|
| C | 58.37% | 58.11% |
| H | 3.81 | 3.98 |
| N | 37.82 | 37.60 |

EXAMPLE 3

4-chlorotetrazolo[1,5-a]quinoxaline

A 3.3 g. portion of anhydrous hydrazine and 10 g. of 2,3-dichloroquinoxaline were refluxed in 200 ml. of methanol for about 20 minutes. The reaction mixture was then allowed to cool, and the intermediate product, 2-chloro-3-hydrazinoquinoxaline, precipitated and was collected by filtration. After the intermediate was washed with water, the yield was 6.7 g. and the melting point was 180°C.(dec.)

The above intermediate product was dissolved in 60 ml. of glacial acetic acid, and 2.39 g. of sodium nitrite in 5 ml. of water was added. The product precipitated immediately. The reaction mixture was chilled for 1 hour, and the product was collected by filtration, washed with water and air dried. Recrystallization from anhydrous ethanol gave 4.8 g. of 4-chlorotetrazolo[1,5-a]quinoxaline, m.p. 194°–96°C. Results of the elemental microanalysis were as follows.

| | Theoretical | Found |
|---|---|---|
| C | 46.73% | 46.81% |
| H | 1.96 | 2.13 |
| Cl | 17.24 | 17.07 |
| N | 34.06 | 34.08 |

The following examples illustrate typical catalytic hydrogenation reactions.

EXAMPLE 4

4,5-dihydrotetrazolo[1,5-a]quinoxaline

A 1 g. portion of tetrazolo[1,5-a]quinoxaline was dissolved in 200 ml. of ethanol. The solution was placed in a Parr hydrogenator on a shaking apparatus and 100 mg. of 5 percent palladized charcoal was added. The bomb was pressurized to about 2 atmospheres with hydrogen and was shaken for 2 hours. The reaction mixture was then removed and filtered. The filtrate was evaporated to dryness and the residue was recrystallized from ethanol-water to obtain the product, 4,5-dihydrotetrazolo[1,5-a]quinoxaline, m.p. 149°–51°C., in 45 percent yield. The product was identified by nuclear magnetic resonance analysis and by elemental microanalysis, with the following results.

| | Theoretical | Found |
|---|---|---|
| C | 55.48% | 55.23% |
| H | 4.07 | 3.88 |
| N | 40.44 | 40.64 |

EXAMPLE 5

4,5-dihydro-4,6-dimethyltetrazolo[1,5-a]quinoxaline

A solution of 1.5 g. of 4,6-dimethyltetrazolo[1,5-a]quinoxaline in 200 ml. of ethanol was hydrogenated as above at about 3 atmospheres over 150 mg. of 5 percent palladized charcoal for 17 hours. The reaction mixture was then filtered, and the filtrate was evaporated to dryness. The residue was taken up in ethyl ether and chromatographed on a silica gel column with ethyl ether as the eluting solvent. The product-containing fractions were evaporated to dryness and the residue was recrystallized from ethanol to recover 4,5-dihydro-4,6-dimethyltetrazolo[1,5-a]quinoxaline, m.p. 159°–61°C., in 81 percent yield. The product was identified by NMR analysis and by elemental analysis with the following results.

| | Theoretical | Found |
|---|---|---|
| C | 59.69% | 59.66% |
| H | 5.51 | 5.33 |
| N | 34.80 | 34.93 |

The next example illustrates the addition of a 5-alkyl substituent.

EXAMPLE 6

4,5-dihydro-5-methyltetrazolo[1,5-a]quinoxaline

A solution of 1 g. of 4,5-dihydrotetrazolo[1,5-a]quinoxaline and 2 g. of methyl iodide in 50 ml. of dimethoxyethane was stirred with 1.5 g. of sodium hydride, as a 50 percent suspension in mineral oil, overnight at room temperature. The reaction mixture was then filtered and evaporated under vacuum. The residue was dissolved in ethyl acetate and extracted twice with water. The brown residue which resulted on evaporation of the dried organic layer was washed with cyclohexane, leaving 0.87 g. of crude product. Two recrystallizations from ethanol produced pure 4,5-dihydro-5-methyltetrazolo[1,5-a]quinoxaline, m.p. 107°–10°C., which was identified by NMR analysis and elemental micro-analysis with the following results.

| | Theoretical | Found |
|---|---|---|
| C | 57.74% | 57.60% |
| H | 4.85 | 4.58 |
| N | 37.41 | 37.66 |

Synthetic methods typified by the above examples, and explained by the above general description, are used to produce all of the compounds, such as the following.

EXAMPLE 7

4,5-dihydro-6-methyltetrazolo[1,5-a]quinoxaline, m.p. 185°–87°C.

EXAMPLE 8

4,5-dihydro-4-methyltetrazolo[1,5-a]quinoxaline, m.p. 127.5°–28°C.

The compounds described above have been shown in a number of in vivo tests to protect plants from the adverse effects of foliar phytopathogens. The following examples illustrate the tests employed and the results produced by representative compounds.

In most of the tests, each compound was formulated for testing by dissolving or suspending about 3.5 weight percent of it in 50:50 acetone:ethanol containing about 10 g./100 ml. of a nonionic surfactant. The solution was then dispersed in deionized water in a quantity such that the water dispersion contained the various compound concentrations indicated in the specific test methods and the tables below. Concentrations are measured in parts per million by weight.

The compound dispersions were applied to the test plants by spraying them with an air atomizer, using sufficient dispersion to wet the plants thoroughly.

Untreated, infected controls and untreated, normal controls were included in each test. The results are reported on a 1–5 rating scale where 1 indicates severe disease and 5 indicates complete control of the disease. An empty space in the tables below shows that the indicated compound was not tested at the indicated rate. In some cases, more than one test was performed against a given phytopathogen, and the results in such cases are reported as averages. Compounds are identified by the example numbers used above.

The following test methods were used.

TEST 1

Helminthosporium Leaf Spot of Wheat

Healthy wheat seed was planted in sterile greenhouse soil. When the seedlings were 4–5 inches tall, they were sprayed with test compound dispersions at compound concentrations indicated in the table below. The day after treatment, the plants were inoculated with a spore suspension of *Helminthosporium sativum* which had been grown on potato dextrose agar. The plants were placed in a moist growth chamber for two days to start disease growth, and were then transferred to the greenhouse. About a week after treatment, the plants were observed and the results were recorded.

TEST 2

Late Blight of Tomato

Four-week-old tomato seedlings were sprayed with aqueous dispersions containing test compounds at compound concentrations indicated in the table below. The following day, the foliage was inoculated with an aqueous suspension of propagules of *Phytophthora infestans*. The inoculum had been reared on infected wheat seed. The plants were held for two days in a moist chamber, and were then transferred to the greenhouse. The plants were observed and rated for disease control about 1 week after application of the test compounds.

TEST 3

Powdery Mildew of Bean

The host plants were 10-day-old bean seedlings. After aqueous dispersions containing test compounds at compound concentrations indicated in the table below had been sprayed on the foliage of the beans and allowed to dry, the plants were placed in the greenhouse and inoculated by storing them under other bean plants which were heavily infected with powdery mildew (*Erysiphe polygoni*). After about 10 days, the plants were observed and the results recorded as usual.

TEST 4

Anthracnose of Cucumber

Aqueous dispersions containing test compounds at compound concentrations indicated in the tables below were applied to healthy cucumber seedlings grown in sterilized greenhouse soil. The following day, the plants were inoculated with *Colletotrichum lagenarium* conidia as an aqueous suspension. The fungus had been grown on potato dextrose agar in petri dishes. The plants were held in a moist chamber for two days and transferred to the greenhouse, and the disease was observed and rated approximately 12 days after application of the test compounds.

TEST 5

Rice Blast of Rice

The test compound dispersions, at compound concentrations indicated in the tables below, were applied to healthy rice seedlings growing thickly in plastic pots. The plants were inoculated on the next day with *Piricularia oryzae* (grown on rice polish agar) and the plants were held in a moist chamber for 2 days. The plants were then held in the greenhouse for 5–7 days and observed.

TEST 6

Bacterial Wilt of Tomato

Tomato seedlings were grown in the greenhouse in plastic pots. When the plants were about 30 days old, aqueous dispersions of the compounds to be tested were sprayed on the treated plants. On the following day, the plants were inoculated with *Pseudomonas solanacearum* by inserting a toothpick, soaked in a bacterial broth culture, at a leaf stem junction. The plants were then moved to the greenhouse, and kept for two days under a translucent plastic hood. The hood was removed on the third day in the greenhouse, and the plants were observed and the results recorded after about 1 week in the greenhouse.

TEST 7

Bacterial Blight of Soybean

Soybean seedlings, about 8 days old, growing in plastic pots were sprayed with aqueous dispersions of the test compounds. On the next day, the treated plants were inoculated by spraying the lower leaf surfaces with a water suspension of *Pseudomonas glycinea*. The plants were then handled as in the test immediately above, except that they were observed about 6 days after inoculation.

Table 1

| Compound | Appln. Rate ppm. | Late Blight | Powdery Mildew | Anthracnose | Rice Blast | Helminthosporium | Bacterial Blight | Bacterial Wilt |
| --- | --- | --- | --- | --- | --- | --- | --- | --- |
| 4,5-dihydro-5-methyltetrazolo-[1,5-a]quinoxaline | 400 | 1 | 2 | | 3 | 1 | | |
| 4,5-dihydro-6-methyltetrazolo-[1,5-a]quinoxaline | 400 | 2 | 1 | 5 | 4.5 | 1 | 1 | 1 |
| | 80 | 1 | | | 1 | | | |
| | 40 | | | | | | | |
| | 16 | 1 | | | 1 | | | |
| 4,5-dihydro-tetrazolo[1,5-a]-quinoxaline | 400 | 2 | 3 | 4 | 4.5 | 1 | 1 | 1 |
| | 80 | | | 3 | 3.5 | | | |

Table 1-continued

| Compound | Appln. Rate ppm. | Late Blight | Powdery Mildew | Anthracnose | Rice Blast | Helminthosporium | Bacterial Blight | Bacterial Wilt |
|---|---|---|---|---|---|---|---|---|
| | 40 | | | | | | | |
| | 16 | | | 1 | 3 | | | |
| | 3.2 | | | 1 | 1 | | | |
| 4,5-dihydro-4-methyltetrazolo-[1,5-a]quinoxaline | 400 | 1 | | 3 | 4.5 | 1 | 1 | 1 |
| | 80 | | | 2 | 2 | | | |
| | 40 | | | | | | | |
| | 16 | | | 1 | 1 | | | |
| 4,5-dihydro-4,6-dimethyltetrazolo-[1,5-a]quinoxaline | 400 | | 1 | 4 | 3 | 1 | 1 | 1 |
| | 80 | | | 3 | 2.5 | | | |
| | 40 | | | | | | | |
| | 16 | | | 2.5 | 2 | | | |
| | 3.2 | | | 1 | 1 | | | |

An important aspect of the invention is a new method of reducing the adverse effects of foliar phytopathogens which comprises contacting the phytopathogens with an effective phytopathogen-inhibiting amount of one of the compounds described above. The method is carried out by applying a compound described above to the foliage of plants, where the compound contacts the phytopathogens. The preferred use of the method is in reducing the adverse effects of phytopathogens, particularly P. oryzae, on the foliage of rice.

Practice of the method does not necessarily kill the contacted phytopathogens. As the data above show, application of a sufficient amount of a compound of the invention to inhibit the phytopathogen reduces the adverse effects of the disease, even though only a part of the phytopathogen population is killed by the compound.

As is usual in the plant protection art, best results are obtained by applying the compound several times during the growing season at intervals of from one to a few weeks, depending on the weather and the severity of the disease.

The methods of formulating the compounds and preparing dispersions of the formulations, and the methods of applying dispersions of the compounds to the plants to be protected, are entirely conventional in the plant protection art. Some explanation of the methods of application will be given merely to assure that those skilled in the art can carry out the invention without undue experimentation.

It is usual in describing foliar applications of plant protectants to measure the application rate by the concentration of the dispersion in which it is applied. The application rate is measured in this way because it is customary to apply a sufficient amount of the dispersion to cover the foliage with a thin film. The amount of dispersion applied is thus dependent on the foliar area of the plants being treated, and the quantity of plant protecting compound is dependent upon its concentration in the dispersion.

Compound concentrations in the range of from about 25 to about 1500 parts of compound per million parts by weight of the dispersion are used in the practice of this invention. Of course, from time to time, higher or lower concentrations will be useful, depending on the severity of the infection and the characteristics of the specific compound in use. The named range, however, encloses the usual optimum concentrations of the compounds.

The dispersions in which the compounds are applied to foliage are most often aqueous suspensions or emulsions prepared from concentrated formulations of the compounds. Such water-suspendible or emulsifiable formulations are either solids usually known as wettable powders or liquids usually known as emulsifiable concentrates. Wettable powders comprise an intimate mixture of the active compound, an inert carrier and surfactants. The concentration of the active compound is usually from about 10 percent to about 90 percent by weight. The inert carrier is usually chosen from among the attapulgite clays, the montmorillonite clays, the diatomaceous earths, or the purified silicates. Effective surfactants, comprising from about 0.5 percent to about 10 percent of the wettable powder, are found among the sulfonated lignins, the condensed naphthalenesulfonates, the naphthalenesulfonates, the alkylbenzenesulfonates, the alkyl sulfates, and nonionic surfactants such as ethylene oxide adducts of alkyl phenol.

Typical emulsifiable concentrates of the compounds comprise a convenient concentration of the compound, such as from about 100 to about 500 g. per liter of liquid, dissolved in an inert carrier which is a mixture of water-immiscible organic solvent and emulsifiers. Useful organic solvents include the aromatics, especially the xylenes, and the petroleum fractions, especially the high-boiling naphthalenic and olefinic portions of petroleum such as heavy aromatic naphtha. Other organic solvents may also be used, such as terpenic solvents including rosin derivatives, and complex alcohols such as 2-ethoxyethanol. Suitable emulsifiers for emulsifiable concentrates are chosen from the same types of surfactants used for wettable powders.

Adjuvants are frequently used to improve the ability of the aqueous dispersion to coat and adhere to foliage. Such adjuvants as gums, emulsified polybutenes, cationic surfactants and lignin derivatives can often increase the potency of the method in a specific use.

Less frequently, the compounds are applied in the form of dusts. Agricultural chemical dusts typically comprise the compound in a finely powdered form, dispersed in a powdered inert carrier. Most often, the carrier is a powdered clay, such as pyrophyllite, bentonite, a volcanic deposit, or montmorillonite. Dusts are usually prepared to contain concentrations of the compound at the highest part of the concentration range, such as 1500 ppm., and may contain even more active ingredient.

Dispersions of the compounds are applied to foliage in the usual manners. Low-pressure sprayers, high-pressure sprayers and low-volume air blast equipment are all effective for the application of water-dispersed compounds of the invention. Dust dispersions are readily applied by means of the usual equipment which blows the dust into intimate contact with the foliage.

We claim:
1. A compound of the formula:

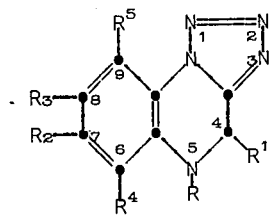

wherein

R and $R^1$ independently represent hydrogen, ethyl or methyl;

$R^2$, $R^3$, $R^4$ and $R^5$ independently represent ethyl, methyl, chloro, fluoro, bromo or hydrogen; provided that at least four of R, $R^1$, $R^2$, $R^3$, $R^4$ and $R^5$ represent hydrogen.

2. A compound of claim 1 which is 4,5-dihydro-5-methyltetrazolo[1,5-a]quinoxaline.

3. A compound of claim 1 which is 4,5-dihydrotetrazolo[1,5-a]quinoxaline.

4. A compound of claim 1 which is 4,5-dihydro-6-methyltetrazolo[1,5-a]quinoxaline.

5. A compound of claim 1 which is 4,5-dihydro-4-methyltetrazolo[1,5-a]quinoxaline.

6. A compound of claim 1 which is 4,5-dihydro-4,6-dimethyltetrazolo[1,5-a]quinoxaline.

* * * * *